United States Patent [19]

Fujiwara et al.

[11] Patent Number: 4,684,738

[45] Date of Patent: Aug. 4, 1987

[54] PROCESS FOR PRODUCING BENZOPHENONE TETRACARBOXYLIC DIANHYDRIDE

[75] Inventors: Shuetsu Fujiwara; Naoki Andoh; Kenji Hosotani, all of Yokohama, Japan

[73] Assignee: Japan Synthetic Rubber Co., Ltd., Tokyo, Japan

[21] Appl. No.: 854,473

[22] Filed: Apr. 22, 1986

[30] Foreign Application Priority Data

Apr. 24, 1985 [JP] Japan .................................. 60-86477

[51] Int. Cl.$^4$ .......................................... C07D 307/89
[52] U.S. Cl. ....................................................... 549/242
[58] Field of Search ............................................ 549/242

[56] References Cited

U.S. PATENT DOCUMENTS 3,850,967 11/1974 Suatoni et al. ...................... 549/242

FOREIGN PATENT DOCUMENTS 420609 8/1974 U.S.S.R. .

OTHER PUBLICATIONS

Zh Org. Khim 4(1) 163–168 (1968).
Chemical Abstract, vol. 68, p. 8374, 1968.
Chemical Abstract, vol. 80, 1974.
Chemical Abstract, vol. 66, p. 7183, 1967.

*Primary Examiner*—Richard L. Raymond
*Attorney, Agent, or Firm*—Oblon, Fisher, Spivak, McClelland & Maier

[57] ABSTRACT

A process for producing benzophenone tetracarboxylic dianhydride, which comprises adding benzophenone tetracarboxylic acid to a solvent comprising, as the main constituent, an organic compound having a boiling point of more than 100° C. and being inert to benzophenone tetracarboxylic acid and benzophenone tetracarboxylic anhydrides, and heating the resulting mixture. This process enables one to produce benzophenone tetracarboxylic dianhydride having a very low moisture absorbency.

15 Claims, 4 Drawing Figures

PROCESS FOR PRODUCING BENZOPHENONE TETRACARBOXYLIC DIANHYDRIDE

BACKGROUND OF THE INVENTION

1. FIELD OF THE INVENTION

This invention relates to a process for producing benzophenone tetracarboxylic dianhydride (hereinafter referred to as BTDA) of low moisture absorbency, which is useful as a starting material for producing polyimides, polyamides and polyesters.

2. DESCRIPTION OF THE PRIOR ART

BTDA was used as a curing agent for epoxy resins, polyurethanes and the like. In recent years, it has gained in importance as a starting material for condensation polymers such as polyimides, polyamides, polyesters and the like. To be useful as a starting material for these polycondensates, BTDA is required to have an extremely high purity, because the polymerization degree of a polycondensate is greatly affected by the purity of monomers. Among the impurities of BTDA, especially harmful are compounds such as carboxylic acids, for example, acetic acid, propionic acid and benzoic acid, and carboxylic anhydrides other than BTDA, for example, acetic anhydride, phthalic anhydride and maleic anhydride, because these compounds act as an end-blocking agent to terminate the polycondensation reaction. When monomers containing a large amount of such impurities are used, the growth of polymer chain is generally hindered to a great extent and the molecular weight adjustment becomes difficult.

The presence of benzophenone tetracarboxylic acid (hereinafter referred to as BTA), which is the free acid of BTDA, is also undesirable, because it causes a decrease in the rate of polycondensation reaction and causes the resulting polymer to be inferior in properties.

BTDA is obtained by dehydrating the above BTA in the manner mentioned below to convert it into anhydride. Benzophenone tetracarboxylic monoanhydride (hereinafter referred to as BTMA) formed by dehydrating only two carboxyl groups as illustrated below also acts as an end-blocking agent in the polycondensation reaction owing to the low condensation reaction activity of the remaining carboxyl groups of these compounds under usual polycondensation conditions.

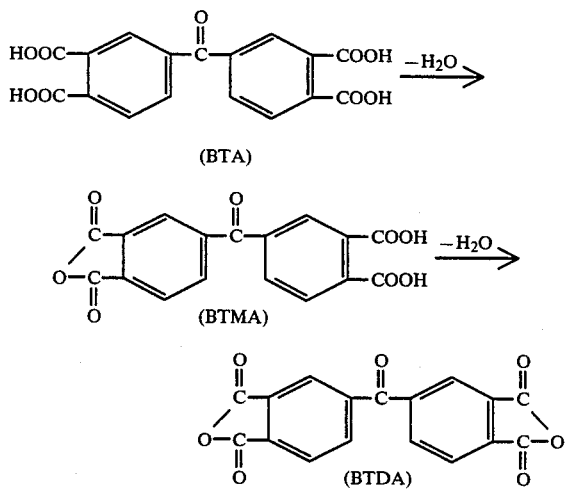

When stored in the atmosphere, BTDA absorbs water to form gradually BTA and BTMA.

BTDA has been known to be produced by the dehydration of BTA as described above. The followings are known as specific procedures to carry out the reaction:

(1) Chemical dehydration by heating BTA in an excess of acetic anhydride [Acetic-anhydride dehydration method, as described, for example, in Zh. Org. Khim 4 (1) 163–168 (1968)].

(2) Dehydration by heating powdered BTA at 200° C. or more under reduced pressure [Method of heating under reduced pressure, Visokomol Soedin, Ser. B 9 (1), 22–23 (1967)].

(3) Dehydration by fluidizing and heating powdered BTA with air heated at 200° C. or more [Fluidizing and heating method, USSR Patent No. 420,609].

However, these known methods have the following problems:

In the case of (1) acetic acid dehydration method, the product BTDA inevitably contains harmful impurities such as the acetic anhydride used, acetic acid formed by the reaction of the acetic anhydride with the water removed from BTA, and the like, and the complete removal of said impurities was practically impossible.

In the case of both (2) method of heating under reduced pressure and (3) fluidizing and heating method, there is available no simple and reliable criterion for the complete conversion of BTA into BTDA, and hence, it follows that the reaction is frequently conducted at too high a temperature or for too long a period of time. Therefore, the resulting BTDA often has a cream to light brown color and the purity thereof is as low as 95 to 98% by weight.

Also, it is known that the BTDA obtained by the method of (1), (2) or (3) tends to absorb water from the atmosphere when stored in a plastic bottle, a fiber drum or the like, upon which the BTDA hydrolyzes into BTA or BTMA and the purity thereof decreases further with the lapse of time.

SUMMARY OF THE INVENTION

The present invention has been made to solve the above-mentioned technical problems and aims at providing a method for producing BTDA having a high purity and an extremely low moisture absorbency.

According to this invention, there is provided a process for producing BTDA, which comprises adding BTA to a solvent comprising as the main constituent an organic compound which is inert to BTA, BTMA and BTDA and which has a boiling point of more than 100° C., and heating the resulting mixture.

DETAILED DESCRIPTION OF THE INVENTION

Figure 1:
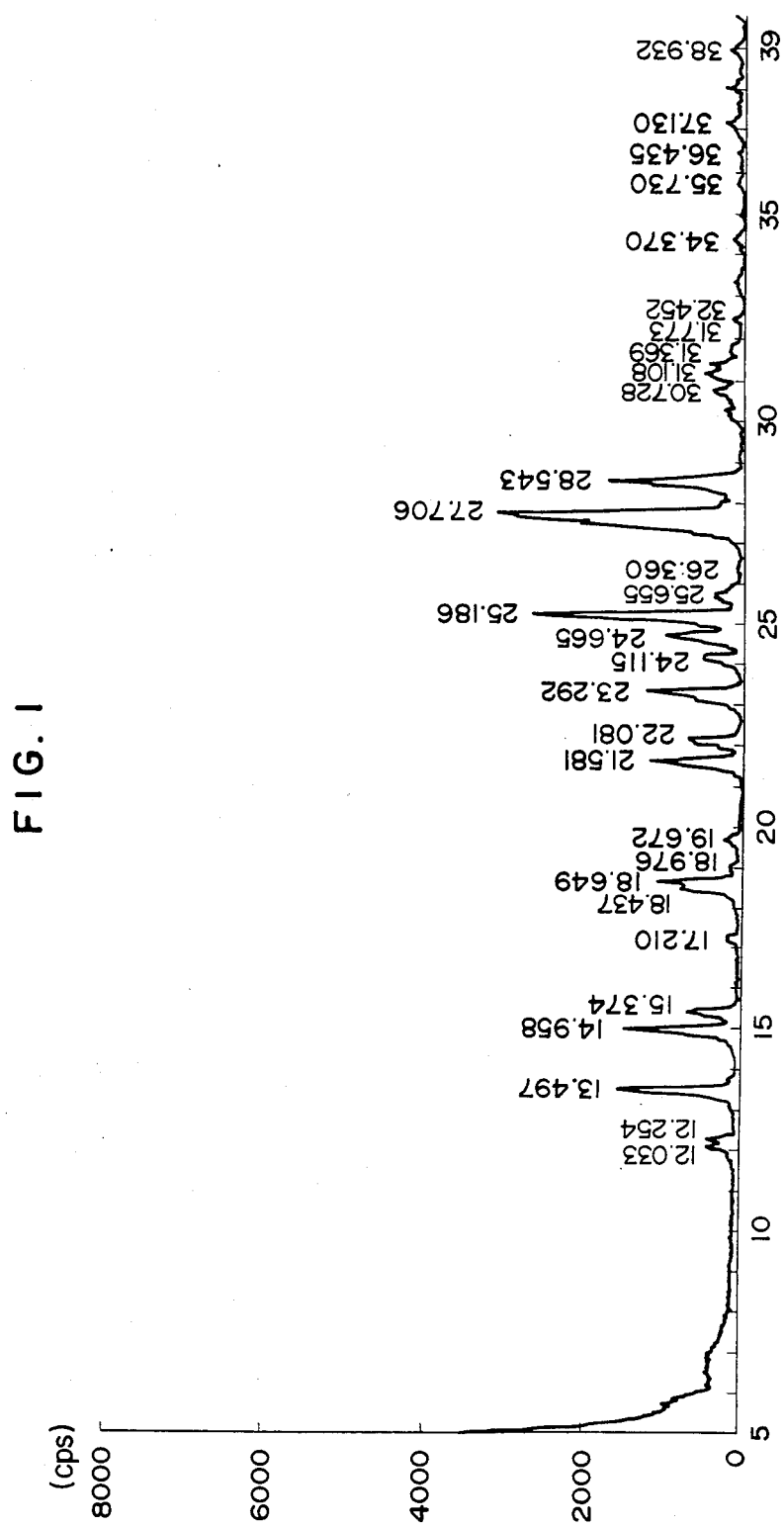
FIGS. 1, 2, 3 and 4 of the accompanying drawings show X-ray diffraction patterns of crystals of BTDA in the A form, the B form, the C form and the D form, respectively.

BTA used as the starting material in this invention can be easily produced, for example, by oxidizing bis(-dimethylphenyl)ethane with nitric acid at an elevated temperature, and the following (a) to (c) methods are specifically used:

(a) Oxidation of bis(dimethylphenyl)ethane with an aqueous nitric acid solution of a concentration of 5 to 60% by weight at a temperature of 100° to 220° C., preferably 120° to 200° C.

(b) Oxidation of bis(dimethylphenyl) ethane with an aqueous nitric acid solution of a concentration of 5 to 60% by weight in the presence of oxygen at 100° to 220° C., preferably 120° to 200° C.

(c) Oxidation of bis(dimethylphenyl)ethane at 100° to 220° C., preferably 120° to 200° C., by gradual feeding of an aqueous nitric acid solution of a concentration of 5 to 60% by weight.

In the above methods (a), (b) and (c), the amount of the aqueous nitric acid solution used is generally 3 to 30 moles, preferably 5 to 15 moles, in terms of 100% nitric acid, per mole of bis(dimethylphenyl)ethane. If the amount of the aqueous nitric acid solution is less than 3 moles, the oxidation will not sufficiently proceed, whereas an amount exceeding 30 moles is not only unnecessary for the reaction, but also causes a disadvantage in the recovery of the resulting BTA from the reaction mixture.

In the (a) method, if an aqueous nitric acid solution of a concentration exceeding 60% by weight is used, the amount of yellow by-products formed becomes large rapidly, whereas if the concentration is less than 5% by weight, it becomes necessary to use a large volume of an aqueous nitric acid solution, resulting in a decrease in productivity of the reactor and an increase in energy consumption for the concentration of the reaction mixture and for the deposition and separation of BTA. Regarding the reaction temperature, the amount of yellow by-products formed increases at less than 100° C. and rapidly decreases at 100° C. or more. At a reaction temperature exceeding 170° C., the yellow by-products formed, though in a small amount, are difficult to remove completely by the recrystallization from water in the subsequent step, and the recrystallized BTA is yellow-collored and it is difficult to obtain white BTA. This seems to be because some of the by-products formed under such conditions have a chemical structure closely resembling that of BTA. Moreover, at a reaction temperature exceeding 220° C., the amount of by-products such as carbon dioxide and the like is increased and the rate of reaction becomes high enough to render the reaction violent and uncontrollable.

The (b) method is specifically carried out in any of the following manners:

(i) The starting compound and the aqueous nitric acid solution are previously charged into the reactor and then the temperature is elevated to cause reaction.

(ii) The aqueous nitric acid solution previously charged into the reactor is heated to a predetermined temperature and then the starting compound is fed thereto by a pump or other means to cause reaction.

(iii) Only a portion or the whole of the water previously charged into the reactor is heated to a predetermined reaction temperature, and then the starting compound and nitric acid or an aqueous nitric acid solution are simultaneously or alternately fed to cause reaction.

In the manner (iii), there may be used an aqueous nitric acid solution of a concentration exceeding 60% by weight, provided that the concentration and quantity of the nitric acid in the reactor after completion of the charging must be in the ranges as mentioned above.

The oxygen to be present in the reaction system can be blown into either the gas phase or the liquid phase in the reactor. The oxygen source may be pure oxygen, air or pure oxygen diluted with a gas such as nitrogen, carbon monoxide, carbon dioxide, nitrous oxide, nitrogen dioxide or the like. The feeding rate of oxygen varies depending upon the factors affecting the rate of reaction such as the ratio between the starting compound and the aqueous nitric acid and the reaction temperature, but it is generally 0.1 to 5 moles/hour, preferably 0.2 to 1 mole/ hour in terms of pure oxygen for 1 mole of the starting compound. If the oxygen-feeding rate exceeds 5 moles/hour, the oxygen-feeding rate becomes excessive as compared with the reaction rate, resulting in a decrease in utilization of oxygen, whereas if the oxygen-feeding rate is less than 0.1 mole/hour, the oxygen-feeding rate becomes deficient against the reaction rate, resulting in an increase in consumption of nitric acid.

In the (b) method, the gases generated from the reaction system during the reaction are the unutilized oxygen introduced into the reactor, nitrogen compounds generated by nitric acid oxydation, carbon monoxide, carbon, dioxide, etc. The nitrogen compounds generated by nitric acid oxydation include nitrogen monoxide, nitrogen dioxide, nitrous oxide, nitrogen, etc. The presence of oxygen in the reaction system greatly inhibits the formation of the nitrogen compounds in the gases generated from the reaction system, particularly nitrogen monoxide, nitrogen dioxide, and the like, resulting in a large decrease in consumption of nitric acid. In carrying out the (b) method, it is desirable to conduct the reaction while releasing the generated gases from the reactor in order to keep the reactor from an increase in internal pressure due to the generated gases. For this purpose, it is necessary to provide the reactor with a cooling pipe, an internal pressure-controlling device to control the pressure of the gases to be withdrawn through the cooling pipe, and other necessary accessories.

The (c) method is specifically carried out in any of the following manners:

(iv) Only the starting compound is previously heated in a reactor to a predetermined reaction temperature, and then an aqueous nitric acid solution is fed to the reactor by a pump or other means to cause reaction.

(v) The starting compound and water are previously heated in a reactor to a predetermined reaction temperature, and then nitric acid is fed to the reactor by a pump or other means to cause reaction.

(vi) The starting compound alone or together with a portion of water is previously heated in a reactor to a predetermined reaction temperature, and then nitric acid and water are simultaneously or alternately fed to the reactor to cause reaction.

In the manners (iv) to (vi), the starting compound or a mixture of the starting compound and water is heated to 100° to 220° C., preferably 120° to 200° C. The average nitric acid- or aqueous nitric acid solution-feeding rate is preferably 1 to 20 moles/hour in terms of 100% nitric acid for 1 mole of the starting compound. If the feeding rate exceeds 20 moles/hour, the control of removal of the heat of reaction and the like tends to become difficult, whereas if it is less than 1 mole/hour, the reaction time becomes prolonged, and the reaction is not effected efficiently.

In the (a) to (c) methods, the reaction pressure is generally 50 kg/cm$^2$G or less, preferably 10 to 50 kg/cm$^2$G. If the pressure exceeds 50 kg/cm$^2$G, the selectivity of the objective product BTA becomes low owing to side reactions such as decomposition and the like, whereas if the pressure is less than 10 kg/cm$^2$G, both side reactions and formation of nitrogen compounds are increased.

The (b) and (c) methods may be combined. In this case, it follows that the (c) method is effected in the presence of oxygen.

In any of the (a) to (c) methods, after completion of the reaction, the reaction mixture is either cooled, concentrated or cooled after concentration to deposit the crude BTA, which is the objective product, from the reaction mixture. The deposited product is collected by a conventional means such as filtration, centrifugation or the like to obtain crystalline solid of crude BTA. This can be purified by recrystallization from a solvent such as water or the like.

The reaction mixture from which the BTA has been removed is generally an aqueous solution containing unreacted nitric acid. This aqueous solution can be either discarded after neutralization with an alkaline substance or reused by recycling it to the oxidation system.

According to this invention, BTA such as obtained as described above is dehydrated in a solvent. The solvent comprises as the main constituent an organic compound having a boiling point of more than 100° C. and a melting point of 100° C. or less, preferably having a boiling point of 180° C. or more and a melting point of 70° C. or less. Said organic compounds include, for example, aromatic compounds, aliphatic hydrocarbons and ether compounds.

The aromatic compound includes, for example, alkylbenzenes such as toluene, xylene, ethylbenzene, diethylbenzene and the like; polyaryl compounds such as phenylxylylethane, bis(methylphenyl)ethane, bis(dimethylphenyl)ethane, phenylxylylpropane, dibenzyltoluene, dibenzylbenzene, diphenyl, ethyldiphenyl, diethyldiphenyl, triethyldiphenyl, diphenylmethane, diphenylethane and the like; naphthalene compounds such as naphthalene, methylnaphthalene, dimethylnaphthalene, diethylnaphthalene and the like. The aliphatic hydrocarbon includes, for example, saturated hydrocarbons such as octane, nonane, decane, undecane, dodecane, eicosane and the like, and the - ether compound includes, for example, anisole, ethyl phenyl ether, diphenyl ether, ethylene glycol dimethyl ether, ethylene glycol diethyl ether, diethylene glycol diethyl ether, propylene glycol dimethyl ether and the like. Of the above compounds, especially preferred are aromatic compounds having 10 to 30 carbon atoms and ether compounds, and they include diphenyl, ethyldiphenyl, diethyldiphenyl, triethyldiphenyl, phenylxylylethane, alkylnaphthalenes, dibenzyltoluene, diphenyl ether and the like. These organic compounds can be used in combination. In particular, a mixture of 70 to 75% by weight of diphenyl ether and 25 to 30% by weight of diphenyl has a melting point lowered to about 12° C. and can be more practically handled about room temperature. Furthermore, the solvents can contain 50% by weight or less, preferably 25% by weight or less, of other compounds including aliphatic and aromatic hydrocarbons having a low boiling point and being inert to BTA, BTMA and BTDA such as benzene, pentane, hexane, heptane, cyclohexane, naphtha and the like.

In this invention, organic compounds active to BTA and BTDA such as those having an amino, hydroxyl, epoxy, carboxyl or ester group and acid anhydrides should not be used. That is to say, compounds having an amino or hydroxyl group readily react with BTA or BTDA to produce amides or esters, respectively; compounds having an epoxy group readily react with BTDA to cause ring opening reaction; compounds having a carboxyl group gives BTDA water to convert it to BTA, whereby the compounds themselves are converted into acid anhydrides; ester compounds undergo ester interchange reaction with BTA and BTDA; acid anhydrides such as acetic anhydride cause an increase in moisture absorbency of BTDA for the above-said reason.

The amount of the solvent used in the dehydration according to this invention is generally 50 to 10,000 parts by weight, preferably 100 to 5,000 parts by weight, per 100 parts by weight of BTA. The amount of the solvent of less than 50 parts by weight is too small to easily agitate the reaction system during the reaction, whereas the amount of the solvent of more than 10,000 parts by weight is too large to make the productivity high.

The dehydration of BTA is allowed to proceed by heating the mixture containing BTA usually at 180° to 250° C., preferably 200° to 250° C., and more preferably 210° to 230° C. In this case, if necessary, the reaction system may be under pressure. If the reaction temperature is less than 180° C., the dehydration is too slow, whereas if the temperature exceeds 250° C., the reaction proceeds too fast or side reactions tend to occur. That is, in the reaction system, water is gradually generated in the form of vapor from the BTA upon heating, and the dehydration becomes gradually active about 180° C. If the reaction temperature is less than 180° C., it takes a too long time for the dehydration to proceed to the desired degree, whereas if the temperature exceeds 250° C., the whole of the reaction system is rapidly boiled up owing to the water generated and this is very dangerous and results in side reactions to color the product BTDA yellow to brown.

The reaction time may be varied depending upon the reaction temperature, the concentration of BTA and the like though it is usually 10 to 300 minutes, and when the reaction temperature is 210° to 230° C. the reaction time is within 60 minutes.

BTA is converted into BTDA which is consequently dissolved in the solvent, and when a major part of BTA has been converted, the reaction system becomes transparent.

In such a dehydration reaction, there is the fear that the steam generated from the reaction system upon dehydration adheres to the wall or the upper part of the reactor and is returned to the reaction system. It is, therefore, preferable to introduce a stream of a noncondensable inert gas such as air or nitrogen, preferably nitrogen, into the reaction system during the dehydration, thereby removing continuously the generated steam from the reaction system. The noncondensable inert gas may be introduced into the reaction system in this stage.

The separation of BTDA from the reaction mixture is effected by, for example, cooling the reaction mixture to a temperature between room temperature and 150° C., preferably between room temperature and 140° C., to deposit BTDA and separating the same. From the aforementioned solvent solution of BTDA, BTDA is easily deposited by cooling the solution. The cooling is preferably conducted gradually while stirring the reaction mixture to deposit crystals of BTDA which is easily separated from the reaction mixture.

In the case of the viscosity of a solvent becomes high at room temperature, and hence, there is a case where the deposition of BTDA is inhibited by the resistance of viscosity. In this case, the viscosity of the solvent can be decreased by diluting the solvent with a substance having a low viscosity and a compatibility with the solvent, such as an aromatic or aliphatic hydrocarbon type solvent having a low boiling point, for example, benzene, toluene, xylene, ethylbenzene, diethylbenzene, pentane, hexane, heptane, cyclohexane or the like to facilitate the deposition of BTDA.

The reaction mixture containing deposited BTDA is separated into a crude crystalline powder having a white to pale yellow color and the mother liquor by subjecting the mixture to a conventional separation means such as a filter or the like. The crude BTDA is purified by washing the same with a good solvent for the mother liquor such as an aromatic or aliphatic hydrocarbon type solvent having a low boiling point and being inert to BTDA, for example, benzene, toluene, pentane, hexane, heptane, naphtha or the like, and drying the washed BTDA to yield purified BTDA. In this case, a solvent having a low boiling point and being inert to BTDA such as acetone, methanol, ethanol, ether, tetrahydrofuran or the like can be used as the solvent; however, BTDA tends to be dissolved in these solvents, and hence, the yield of BTDA becomes low in some cases.

The present BTDA obtained as described above has a high purity of at least 99.5% by weight and a melting point of about 224.5–225.5° C. as compared with a commercial product which has a purity of about 97% by weight and a melting point of about 220° C.

The crystals of the BTDA obtained according to this invention have usually a particle diameter of 10 to 300 μm, and many of them have the shape of plate or parallelepiped. The X-ray diffraction analysis of these BTDA crystals has confirmed four crystal forms of BTDA.

Figure 2:
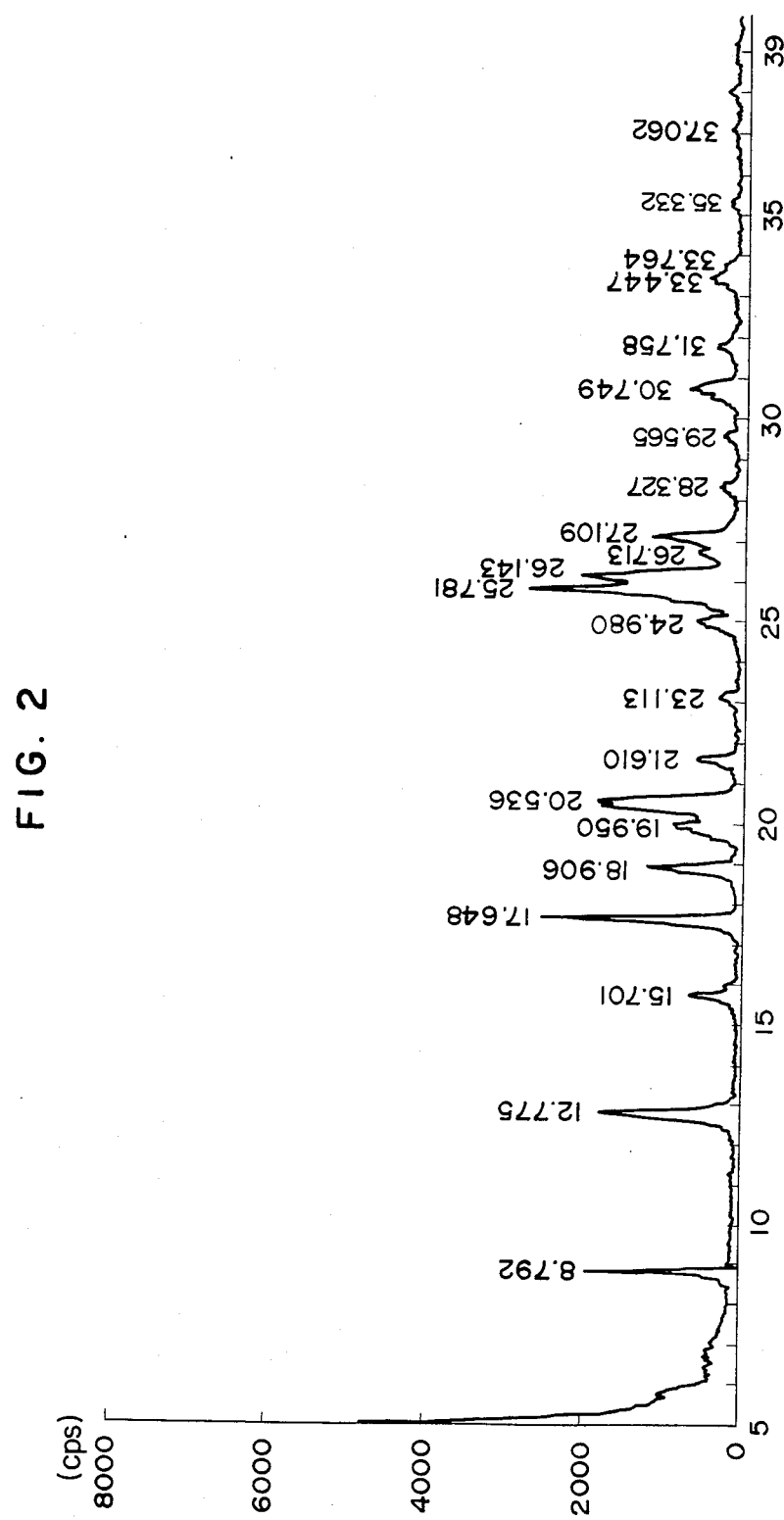
Figure 3:
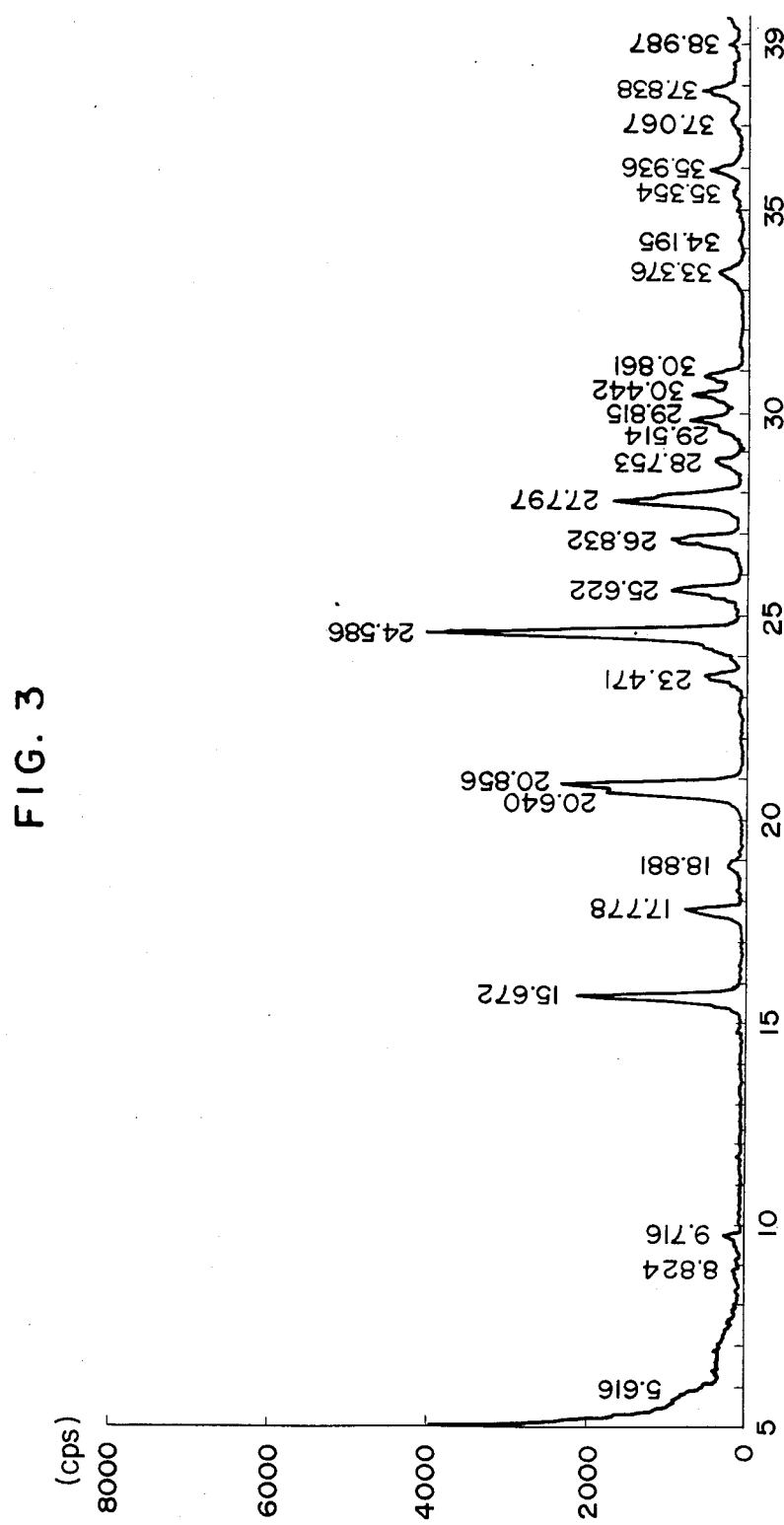
Figure 4:
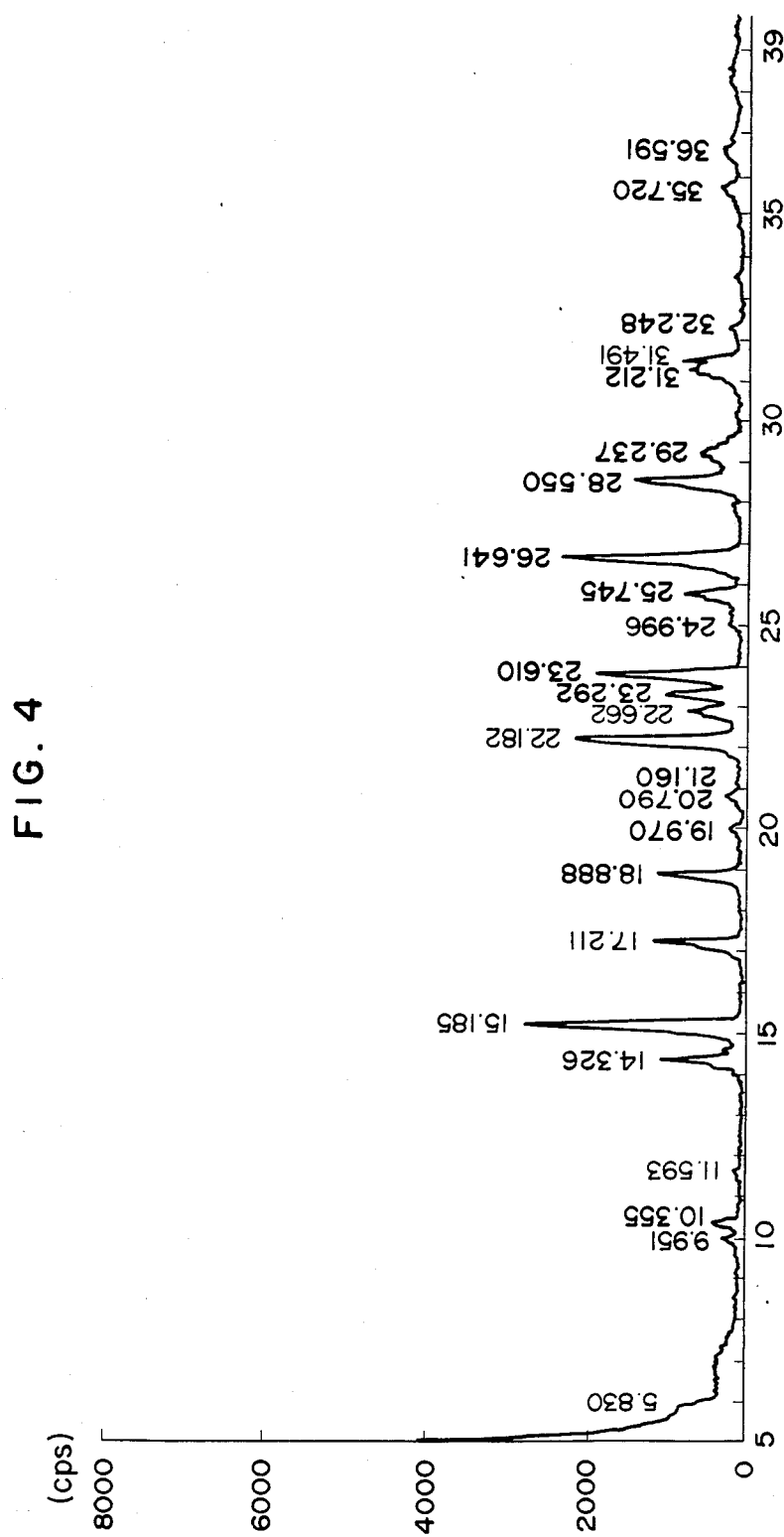

FIGS. 1 to 4 show X-ray diffraction patterns of the four crystal forms (A, B, C and D forms). The X-rays used in the measurement were $CuK_{60}$ rays and the measurement apparatus was an X-ray diffraction apparatus of the RAD-rA type of Rigaku Denki. The four forms are designated as A, B, C and D. The diffraction angle ($2\theta$) of each X-ray diffraction pattern is as follows:

The A form has characteristic peaks at 13.5, 15.0, 18.6, 23.3, 25.2, 27.8 and 28.6, The B form has characteristic peaks at 8.8, 12.8, 17.7, 18.9, 20.5, 25.8, 26.1 and 27.1, The C form has characteristic peaks at 15.7, 17.8, 20.6, 20.9, 24.6, 25.6, 26.8 and 27.8, The D form has characteristic peaks at 15.2, 17.2, 18.9, 22.2, 23.6, 26.6 and 28.6.

(The error of determination of diffraction angle is usually 1% or less than 1%.)

The crystal form of BTDA varies depending upon the conditions of crystallization, and particularly, the type of solvent affects it greatly. When the same solvent is used, there is a tendency to obtain the same crystal form of BTDA. It is possible to always obtain the same crystal form by using the same crystallization conditions.

The most important feature of the BTDA obtained by this invention is a distinguished storage stability as evidenced by the markedly smaller rate of conversion into BTA or BTMA caused by the moisture absorption during storage, as compared with conventional products. For instance, when the BTDA crystals obtained by the method of this invention and a commercial product are allowed to stand in the atmosphere and the weight increase is measured at regular intervals, the rate of weight increase, (weight increase in g)/(initial weight in g)×(time of storage in hour), is as low as about one-tenth to one-hundredth of that of the commercial product. Although the exact reason for the extremely low moisture absorbency of the present BTDA is yet to be elucidated, it seems that the low moisture absorbency is attributable to the crystals of uniformly dehydrated product. For the purpose of examining the relationship between the rate of moisture absorption and the specific surface area of BTDA crystals, a comparative test was run on a sample of the present BTDA having approximately the same particle size as that of the commercial product and a sample of the present BTDA crushed to approximately the same particle size as that of the commercial product. Both samples were found to have a moisture absorbency which is one-tenth to one-hundredth of that of the commercial product, indicating that the moisture absorption of the present BTDA is not affected by the specific surface area of crystals.

DESCRIPTION OF PREFERRED EMBODIMENTS

This invention is illustrated in detail below referring to Examples, wherein percentages are by weight and pressures are gage pressures.

EXAMPLE 1

Into a 1-liter autoclave provided with a gas inlet and a gas outlet were charged 50 g (0.210 mole) of 1,1-bis(3,4-dimethylphenyl)ethane of 98% purity and 600 g (2.858 moles) of a 30% by weight aqueous nitric acid solution. Oxygen was introduced thereinto through the gas inlet to adjust the pressure of the reaction system to 20 kg/cm². While this pressure was minitained the temperature of the reaction mixture was gradually elevated with stirring from room temperature to 120° C. over a period of 1 hour while feeding oxygen at a rate of 400 ml/minute (0° C., 1 atm.) under pressure. After the reaction system had been kept for about 1 hour at 120° C., the temperature was elevated to 180° C. over a period of about 1 hour. The autoclave was kept stirred for about 2 hours at 180° C., while keeping the internal pressure at 20 kg/cm² by feeding oxygen.

Subsequently, the reaction mixture was concentrated to about 300 g by distillation and then cooled down to room temperature. After having been allowed to stand overnight, the reaction mixture was filtered under reduced pressure to collect the deposited crystalline solid. The crystalline solid was washed with about 200 ml of water and dried overnight at 125° C. to yield 59.6 g of crude 3,3′,4,4′-benzophenone tetracarboxylic acid having a purity of 98% or more as determined by liquid chromatography.

Into a 500-ml round bottom flask provided with a thermometer and a narrow tube for introducing nitrogen stream was charged 50 g of the thus obtained BTA, followed by adding thereto a mixed solvent (m.p. 12° C.) consisting of 183.8 g of diphenyl ether and 66.2 g of diphenyl. The temperature of the mixture was elevated from room temperature up to 220° C. over a period of 30 minutes, while introducing nitrogen at a rate of 100 ml/minute through the narrow inlet tube and stirring with a magnetic stirrer. The narrow tube for introducing nitrogen was adjusted so that it might open near the surface of the starting mixture. After 28 minutes of continued stirring at 220° C., the reaction system changed from a suspension to a transparent solution and the tiny bubbles of water vapor generated by the dehydration reaction were rapidly decreased in number. After having been kept at 220° C. for an additional 12 minutes (a total of 40 minutes at 220° C.), the reaction mixture was allowed to cool while being stirred. When the reaction mixture had cooled down to about 140° C., BTDA began to crystallize out. After the temperature had been lowered to about 40° C., the reaction mixture was filtered under reduced pressure to collect crude crystalline BTDA. The crude BTDA was placed in 300 ml of toluene, stirred for 15 minutes, and filtered under reduced pressure. Such a treatment was repeated twice. The washed crystals of BTDA were dried for 1 hour in a dryer kept at 110° C., then in a vacuum desiccator for 1 hour to obtain 44.5 g (99% yield on molar basis) of BTDA.

The crystals of purified BTDA were of the parallelepiped shape as observed under an optical microscope, and the longest particle diameter was 100 to 500 μm. The crystals were ground in a mortar and subjected to X-ray diffraction analysis by using $CuK_\alpha$ rays. The same diffraction pattern was obtained as that of the A form shown in FIG. 1. Upon examination by liquid chromatography, the presence of BTA or BTMA in purified BTDA was not detected.

The purified BTDA was esterified by heating in methanol. After removal of methanol by evaporation, the residue was dissolved in tetrahydrofuran and the remaining carboxyl groups were converted into methyl ester with diazomethane. The purity of the resulting tetramethyl ester of BTA was 99.8% or more, as examined by gas chromatography.

EXAMPLE 2

Into a 500-ml round bottom flask provided with a thermometer and a narrow pipe for introducing nitrogen was charged 50 g of dried BTA obtained in the same manner as in Example 1. After addition of 250 g of dibenzyltoleuen, the reaction mixture was heated with stirring to 230° C. in the same manner as in Example 1. After 7 minutes from the time when the temperature of the mixture had reached 230° C., the starting mixture in the form of suspension changed to a transparent solution and the liberation of water vapor ceased. The mixture was kept at 230° C. for an additional 23 minutes (a total of 30 minutes at 230° C.) and then allowed to cool while being stirred. When the temperature had been lowered to about 180° C., BTDA began to crystallize out of the mixture. After the temperature had reached 30° C., the reaction mixture was filtered under reduced pressure to collect crude crystals of BTDA. In the same manner as in Example 1, the crude crystals were washed with toluene and dried to yield 44.3 g (98.5% yield on molar basis) of purified BTDA in the form of plate crystals having a longest particle diameter of about 250 to about 300 μm. The X-ray diffraction pattern was the same as that of the B form shown in FIG. 2. BTA or BTMA in purified BTDA was not detected by liquid chromatography. Upon examination of the methyl ester by gas chromatography, the purity of purified BTDA was found to be 99.8% or more.

EXAMPLE 3

The BTA obtained by repeating the procedure of Example 1 was dehydrated in the same manner as in Example 1, except that the mixture in the flask was kept at 220° C. for 40 minutes and rapidly cooled by dipping the flask in an iced water bath. The crude BTDA crystals were washed with toluene and dried to obtain purified BTDA crystals having a longest particle diameter of 10 to 17 μm, indicating a smaller average size as compared with that of crystals obtained in Example 1. The X-ray diffraction pattern was the same as that of the A form shown in FIG. 1.

EXAMPLE 4

The same procedure as in Example 2 was repeated, except that diethyldiphenyl was used in place of the dibenzyltoluene. In the same manner as in Example 2, the reaction mixture was allowed to cool and when the temperature had been lowered to about 180° C., BTDA began to crystallize out of the reaction mixture. The amount of the BTDA obtained was 44.5 g (99.0% yield on molar basis). The BTDA crystals were found to have the shape of parallelepiped, a longest particle diameter of 50 to 80 μm, and the same X-ray diffraction pattern as that of the C form in FIG. 3.

EXAMPLE 5

The same procedure as in Example 2 was repeated, except that 1,1-bis(3,4-dimethylphenyl)ethane was used in place of the dibenzyltoluene. The BTDA began to crystallize out of the reaction mixture when the reaction mixture had been cooled to 200° C., whereby 44.1 g (98.0% molar yield) of BTDA was obtained. The BTDA crystals were of the parallelepiped shape having a longest particle diameter of 150 to 260 μm. The X-ray diffraction pattern was the same as that of the D form shown in FIG. 4.

TEST EXAMPLE 1

50 g of each of the BTDA samples obtained in Examples 1 to 5 and two commercial BTDA samples A and B was placed in respective Petri dishes, then precisely weighed, and placed in a desiccator containing a beaker filled with distilled water. The desiccator was closed and kept at a constant temperature of 23° C. The weight of each dish was measured at regular intervals to determine the rate of weight increase. The results were as shown in the Table. Samples A and B were the product of Arco Co. of USA.

$$\text{Rate of weight increase (\%)} = \frac{\text{Weight increase (g)}}{\text{Initial weight (g)}} \times 100$$

The results shown in the Table prove that BTDA obtained according to the present invention has a very low moisture absorbency.

EXAMPLE 6

40 g of BTDA obtained in each of Examples 1 and 2 was ground in a small ball mill for 2 hours under a stream of dried nitrogen to keep BTDA from absorption of water from the atmosphere. After the 2 hours' grinding, the BTDA crystals of Examples 1 and 2 were ground to a longest particle diameter of 5 to 10 μm (Powdered Sample 1) and 7 to 13 μm (Powdered Sample 2), respectively. The samples were tested, in a manner similar to that in Test Example 1, for the weight increase due to moisture absorption. The results obtained were as shown in the Table. From the Table, it is seen that the crystals of the BTDA obtained according to this invention showed a moisture absorbency which is not much affected by pulverization and a much lower moisture absorbency than that of commercial product having approximately the same size.

TABLE

Weight increase of various samples

| Sample | Longest particle diameter (μm) | Weight increase (%) After 1 day | After 4 days | After 14 days |
| --- | --- | --- | --- | --- |
| Example 1 | 100–500 | 0.20 | 1.18 | 1.47 |
| Example 2 | 250–300 | 0.31 | 1.52 | 2.41 |
| Example 3 | 10–17 | 0.17 | 1.05 | 1.29 |
| Example 4 | 50–80 | 0.36 | 0.95 | 1.55 |
| Example 5 | 100–200 | 0.19 | 0.38 | 0.80 |
| Sample A | 5–10 | 8.4 | 18.3 | 20.7 |
| Sample B | 5–10 | 12.3 | 20.4 | 21.2 |
| Example 6 | | | | |
| Powdered Sample 1 | 5–10 | 0.24 | 1.24 | 1.61 |
| Powdered Sample 2 | 7–13 | 0.97 | 2.27 | 2.80 |

What is claimed is:

1. A process for producing benzophenone tetracarboxylic dianhydride, which comprises adding benzophenone tetracarboxylic acid to a solvent comprising, as the main constituent, an organic compound having a boiling point of more than 100° C. and being inert to benzophenone tetracarboxylic acid and benzophenone tetracarboxylic anhydrides, said organic compound being at least one compound selected from the group consisting of alkylbenzenes, naphthalene compounds, polyaryl compounds, aliphatic hydrocarbons, and ether compounds, heating the resulting mixture at a temperature of from 180°–250° C., cooling said mixture to thereby deposit crystals of benzophenone tetracarboxylic dianhydride, and separating said crystals of benzophenone tetracarboxylic dianhydride.

2. A process according to claim 1, wherein said cooling is effected at a temperature of 150° C. or less.

3. A process according to claim 1, wherein the organic compound has a melting point of 100° C. or less.

4. A process according to claim 1, wherein the organic compound has a boiling point of 180° C. or more and a melting point of 70° C. or less.

5. A process according to claim 4, wherein the organic compound is a mixture of 70–75% by weight of diphenyl ether and 25–30% by weight of diphenyl.

6. A process according to claim 1, wherein the organic compound is selected from the alkylbenzenes.

7. A process according to claim 6, wherein the alkylbenzenes are selected from the group consisting of toluene, xylene, ethylbenzene and diethylbenzene.

8. A process according to claim 1, wherein the organic compound is selected from the naphthalene compounds.

9. A process according to claim 8, wherein the naphthalene compounds are selected from the group consisting of naphthalene, methylnaphthalene, dimethylnaphthalene and diethylnaphthalene.

10. A process according to claim 1, wherein the organic compound is selected from the polyaryl compounds.

11. A process according to claim 10, wherein the polyaryl compounds are selected from the group consisting of diphenyl, ethyldiphenyl, diethyldiphenyl, triethyldiphenyl, diphenylmethane, diphenylethane, phenylxylylethane, bis(methylphenyl)ethane, bis(dimethylphenyl) ethane, phenylxylylpropane, dibenzyltoluene and dibenzylbenzene.

12. A process according to claim 1, wherein the organic compound is selected from the aliphatic hydrocarbons.

13. A process according to claim 12, wherein the aliphatic hydrocarbons are selected from the group consisting of octane, nonane, decane, undecane, dodecane and eicosane.

14. A process according to claim 1, wherein the organic compound is selected from the ether compounds.

15. A process according to claim 14, wherein the ether compounds are selected from the group consisting of anisole, ethyl phenyl ether, diphenyl ether, ethylene glycol dimethyl ether, ethylene glycol diethyl ether, diethylene glycol diether ether, and propylene glycol dimethyl ether.

* * * * *